(12) United States Patent
Luttropp et al.

(10) Patent No.: US 8,696,909 B2
(45) Date of Patent: Apr. 15, 2014

(54) HYBRID BIOARTIFICIAL KIDNEY

(75) Inventors: David Luttropp, Frankfurt (DE); Bernd Krause, Rangendingen (DE); Markus Neubauer, Balingen (DE); Reinhold Deppisch, Hechingen (DE); Doris Deppisch, legal representative, Hechingen (DE); Andrea Schnell, Bishingen-Thanheim (DE); Helmut Geiger, Wehrheim (DE); Juergen Bereiter-Hahn, Hofheim (DE); Patrick Baer, Darmstadt (DE)

(73) Assignee: Gambro Lundia AB, Lund (SE)

( * ) Notice: Subject to any disclaimer, the term of this patent is extended or adjusted under 35 U.S.C. 154(b) by 264 days.

(21) Appl. No.: 13/120,298

(22) PCT Filed: Sep. 23, 2009

(86) PCT No.: PCT/EP2009/006860
§ 371 (c)(1),
(2), (4) Date: Apr. 27, 2011

(87) PCT Pub. No.: WO2010/034475
PCT Pub. Date: Apr. 1, 2010

(65) Prior Publication Data
US 2012/0067815 A1      Mar. 22, 2012

(30) Foreign Application Priority Data
Sep. 25, 2008   (EP) .................................... 08016833

(51) Int. Cl.
| | | |
|---|---|---|
| A61M 1/18 | (2006.01) | |
| A61M 1/34 | (2006.01) | |
| B01D 61/24 | (2006.01) | |
| B01D 61/28 | (2006.01) | |
| B01D 63/04 | (2006.01) | |
| B01D 71/76 | (2006.01) | |
| B01D 71/82 | (2006.01) | |
| C12M 3/04 | (2006.01) | |
| C12M 3/06 | (2006.01) | |

(52) U.S. Cl.
USPC ........... 210/646; 210/200; 210/201; 210/202; 210/252; 210/321.6; 210/321.72; 210/321.79; 210/321.8; 210/321.88; 210/321.89; 210/323.1; 210/323.2; 210/483; 210/488; 210/490; 210/500.24; 210/506; 427/487; 427/488; 427/491; 427/496; 427/551; 427/569; 427/595; 435/7.21; 435/400; 435/401; 604/4.01; 604/5.01; 604/5.04; 604/6.09; 604/28

(58) Field of Classification Search
USPC ......... 210/645, 646, 650, 651, 200, 201, 202, 210/252, 321.6, 321.72, 321.79, 321.8, 210/321.88, 321.89, 323.1, 323.2, 483, 488, 210/489, 490, 500.2, 501, 506; 427/487, 427/488, 489, 490, 500.24, 501, 506; 604/4.01, 5.01, 5.04, 6.09, 28; 435/7.21, 396, 400, 401
See application file for complete search history.

(56) References Cited

U.S. PATENT DOCUMENTS 4,056,467 A    11/1977   Christen et al.
(Continued)

FOREIGN PATENT DOCUMENTS

EP        0 362 588 A1     4/1990
(Continued)

OTHER PUBLICATIONS

English translation of EP 0550798 A1.*
(Continued)

*Primary Examiner* — John Kim
(74) *Attorney, Agent, or Firm* — Barnes & Thornburg LLP

(57) ABSTRACT

A bioartificial kidney equivalent and a process for producing the bioartificial kidney equivalent. The hybrid bioartificial kidney comprises human proximal and distal renal tubule cells grown on particular synthetic membranes.

20 Claims, 1 Drawing Sheet

(56) References Cited

U.S. PATENT DOCUMENTS

| | | | |
|---|---|---|---|
| 4,268,662 A * | 5/1981 | Sano et al. | 528/486 |
| 4,749,619 A | 6/1988 | Angleraud | |
| 4,935,141 A * | 6/1990 | Buck et al. | 210/500.38 |
| 5,151,227 A | 9/1992 | Nguyen et al. | |
| 5,369,012 A | 11/1994 | Koontz et al. | |
| 5,431,817 A | 7/1995 | Braatz et al. | |
| 5,686,289 A | 11/1997 | Humes et al. | |
| 5,891,338 A * | 4/1999 | Bell et al. | 210/500.32 |
| 5,954,966 A * | 9/1999 | Matsuura et al. | 210/640 |
| 6,103,117 A | 8/2000 | Shimagaki et al. | |
| 6,150,164 A | 11/2000 | Humes | |
| 6,942,879 B2 * | 9/2005 | Humes | 424/529 |
| 6,960,297 B2 | 11/2005 | Kozawa et al. | |
| 7,470,368 B2 | 12/2008 | Sugaya et al. | |
| 7,837,042 B2 | 11/2010 | Yokota et al. | |
| 8,251,941 B2 * | 8/2012 | Humes et al. | 604/6.03 |
| 8,425,446 B2 * | 4/2013 | Humes et al. | 604/6.03 |
| 8,435,751 B2 * | 5/2013 | Zweigart et al. | 435/7.21 |
| 2003/0021826 A1 | 1/2003 | Crost et al. | |
| 2003/0203478 A1 | 10/2003 | Cadwell | |
| 2004/0062809 A1 | 4/2004 | Honiger et al. | |
| 2005/0045554 A1 * | 3/2005 | Moachon et al. | 210/500.23 |
| 2005/0238687 A1 * | 10/2005 | Humes | 424/423 |
| 2005/0274665 A1 * | 12/2005 | Heilmann et al. | 210/321.8 |
| 2006/0191844 A1 | 8/2006 | Mahuchi et al. | |
| 2006/0234582 A1 | 10/2006 | Gohl et al. | |
| 2007/0082393 A1 * | 4/2007 | Lodhi et al. | 435/325 |
| 2007/0269489 A1 | 11/2007 | Humes | |
| 2010/0016778 A1 * | 1/2010 | Chattopadhyay | 604/6.09 |
| 2010/0163488 A1 * | 7/2010 | Fislage et al. | 210/646 |
| 2010/0326915 A2 * | 12/2010 | Fislage et al. | 210/646 |

FOREIGN PATENT DOCUMENTS

| | | |
|---|---|---|
| EP | 0 550 798 A1 | 7/1993 |
| EP | 0 925 826 A1 | 6/1999 |
| EP | 1 439 212 A1 | 7/2004 |
| EP | 1 875 957 A1 | 7/2006 |
| EP | 1 795 254 A1 | 6/2007 |
| EP | 1875957 | 9/2008 |
| EP | 2 133 298 A1 | 4/2009 |
| EP | 2113298 | 4/2009 |
| EP | 2 113 298 A9 | 11/2009 |
| EP | 1 578 521 B1 | 8/2010 |
| EP | 1578521 | 8/2010 |
| JP | 2003-245526 A | 9/2003 |
| JP | 2004305840 A | 11/2004 |
| WO | 89/01967 A1 | 3/1989 |
| WO | WO89/16967 | 3/1989 |
| WO | 90/11820 A2 | 10/1990 |
| WO | 93/00439 A1 | 1/1993 |
| WO | 01/54802 A1 | 8/2001 |
| WO | 01/56549 A1 | 8/2001 |
| WO | WO01/54802 | 8/2001 |
| WO | 02/00775 A1 | 1/2002 |
| WO | 2004/056459 A1 | 7/2004 |
| WO | 2004/056460 A1 | 7/2004 |
| WO | WO2004/056459 | 7/2004 |
| WO | WO2004/056460 | 7/2004 |
| WO | 2005/021139 A1 | 3/2005 |
| WO | 2006/135966 A1 | 12/2006 |
| WO | 2006/138537 A2 | 12/2006 |
| WO | WO2006/138537 | 12/2006 |
| WO | 2007/148147 A1 | 12/2007 |
| WO | 2008/046779 A1 | 4/2008 |
| WO | 2010/034466 A1 | 4/2010 |
| WO | 2010/034468 A1 | 4/2010 |
| WO | 2010/034469 A1 | 4/2010 |
| WO | 2010/034475 A1 | 4/2010 |
| WO | WO2010/034466 | 4/2010 |
| WO | WO2010/034468 | 4/2010 |
| WO | WO2010/034469 | 4/2010 |

OTHER PUBLICATIONS

Aebischer et al., "Renal Epithelial Cells Grown on Semipermeable Hollow Fibers as a Potential Ultrafiltrate Processor", vol. XXXiii Trans Am Soc Artif Intern Organs, 1987, pp. 96-102.

Aebischer et al., "The Bioartificial Kidney: Progress towards an Ultrafiltration Device with Renal Epithelial Cells processing", Life Support Systems (1987), 5, 159-168.

Andrade et al., "Surface Characterization of Poly(Hydroxyethyl Methacrylate) and Related Polymers. I. Contact Angle Methods in Water", Journal of Polymer Science: Polymer Symposium 66, 313-336 (1979).

Anthony Atala, "Recent developments in tissue engineering and regenerative medicine", Current Opinion in Pediatrics, 2008, 18:167-171.

Baer et al., "Isolation of proximal and distal tubule cells from human kidney by immunomagnetic separation", Kidney International, vol. 52 (1997), pp. 1321-1331.

Fey-Lamprecht et al., "Functionality of MDCK kidney tubular cells on flat polymer membranes for biohybrid kidney", Journal of Materials Science: Materials in Medicine 9 (1998) 711-715.

William H. Fissell, "Developments towards an artificial kidney", Future Drugs Ltd., 2006, 155-165.

Green et al., "Measurement of the Transmittance Coefficient Spectrum of Cuprophan and RP69 Membranes: Applications to Middle Molecule Removal via Ultrafiltration", vol. XXII Trans. Amer. Soc. Artif. Int. Organs, 1976, pp. 627-636.

Humes et al., "The bioartificial kidney in the treatment of acute renal failure", Kidney International, vol. 61, Supplement 80 (2002), pp. S121-S125.

Humes et al., "Tissue engineering of a bioartificial renal tubule assist device: In vitro transport and metabolic characteristics", Kidney International, vol. 55 (1999), pp. 2502-2514.

Akira Saito, "Research into the development of a Wearable Bioartificial Kidney with a Continuous Hemofilter and a Bioartificial Tubule Device Using Tubular Epithelial Cells", Artificial Organs, 28(1):58-63, 2004.

Saito et al., "Present Status and Perspective of the Development of a Bioartificial Kidney for Chronic Renal Failure Patients", Therapeutic Apheresis and Dialysis, 10(4):342-347, 2006.

Sciarratta et al., "Plasma functionalization of polypropylene with acrylic acid", Surface and Coatings Technology 174-175- (2003) 805-810.

International search report from PCT/EP2009/006847 completed Nov. 24, 2009, 10 pages.

International search report from PCT/EP2009/006850 completed Jan. 5, 2010, 9 pages.

International search report from PCT/EP2009/006860 completed Dec. 4, 2009, 10 pages.

International search report for PCT/EP2009/006849, completed Nov. 2, 2009.

International Search Report/Written Opinion for PCT/EP2009/006860, completed Dec. 4, 2009.

Humes et al., 1999, "Replacement of Renal Function in Uremic Animals with a Tissue-Engineered kidney", Nature Biotechnology, 17, 451-455.

* cited by examiner

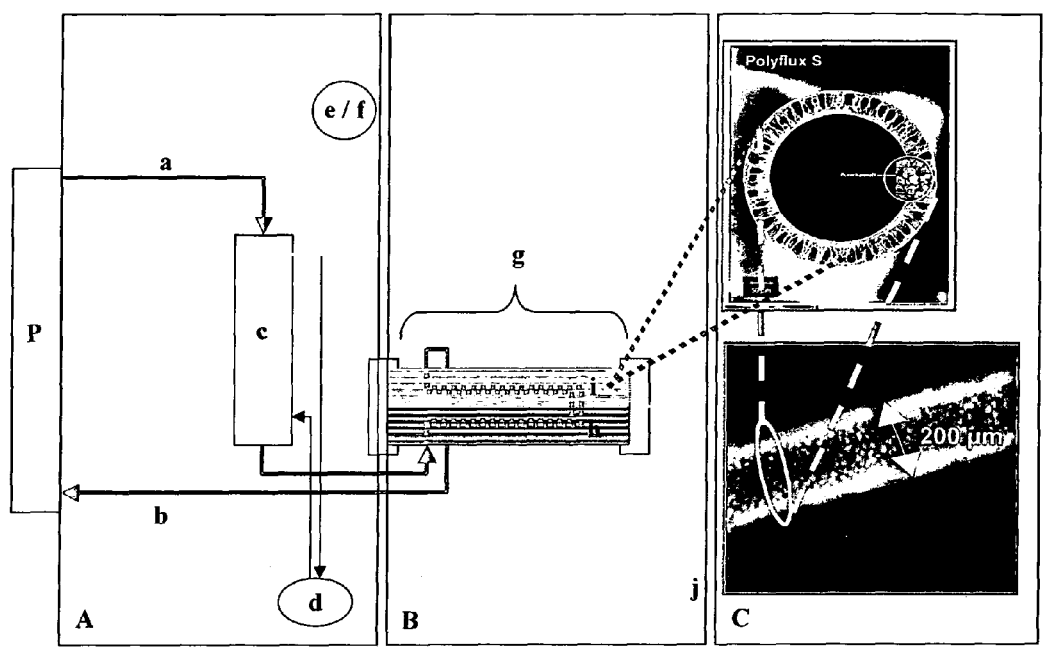

HYBRID BIOARTIFICIAL KIDNEY

CROSS-REFERENCE TO RELATED APPLICATIONS

This application is the U.S. national phase of PCT/EP2009/006860 filed Sep. 23, 2009. PCT/EP2009/006860 claims priority to European patent application 08016833.9 filed Sep. 25, 2008. The disclosures of both European patent application 08016833.9 and PCT/EP2009/006860 are hereby incorporated herein by reference.

TECHNICAL FIELD

The invention relates to a bioartificial kidney equivalent and a process for producing same. The hybrid bioartificial kidney comprises human proximal and distal renal tubule cells grown on particular synthetic membranes.

BACKGROUND OF THE INVENTION

The kidney was the first organ whose function was approximated by a machine and a filter device, and was also the first organ which was successfully transplanted. However, the lack of widespread availability of transplantable organs reserved the rights for transplantation only to patients with chronic renal failure.

The development of acute renal failure (ARF) in a hospitalized patient results in a 5-fold to 8-fold higher risk of death. Although hemodialysis, hemofiltration and peritoneal dialysis treatment with its small solute and fluid clearance function has prevented death from hyperkalemia, volume overload and uremic complications, such as pericarditis, patients with ARF still have mortality rates exceeding 50. It is not a complete renal replacement therapy because it only provides filtration function and does not replace the hemostatic, regulatory, metabolic, and endocrine function. Patients with end stage renal disease on dialysis continue to have major medical, social and economic problems.

Therefore, it is important to invest into the improvement and the development of alternatives to the existing therapies. "Bioartificial" or "hybrid" organs are a promising and realistic alternative to the presently available therapies for the treatment of renal failure.

Acute renal failure as a secondary effect of ischemic and/or nephrotoxic causes arises from acute tubular necrosis (ATN), predominantly to renal proximal tubule cells. A support of these tubular cells and thus a naturally replacement in function during the first time of ATN could provide almost full renal replacement therapy in conjunction with hemofiltration. Additionally with such a support the other main functions of these cells, their metabolic activity such as ammoniagenesis and glutathione reclamation, endocrine activity such as vitamin D3 activation and cytokine homeostasis, may provide additional physiologic replacement activities that have the potential to change the current natural history of this disease process.

The knowledge of the cellular and molecular basis of organ function and diseases will be transferred in the next years into new therapeutic approaches. Central to these are the developing fields of gene therapy, cell therapy and tissue engineering. These new potentialities are based on the ability to expand stem or progenitor cells in tissue culture to perform different tasks and to introduce these cells into the patient either in extra-corporeal circuits or as implantable constructs.

Cell therapy is a new and exciting approach to the treatment off acute and chronic diseases. The potential success of such new ways lies in the growing appreciation that most diseases are not due to the lack or excess of single events but develop due to alterations in the complex interactions of a variety of cell products. In addition, cells organs and tissue need a specific individualized therapy that responds to the pathophysiological conditions. This form of treatment is dependent on cell and tissue culture methodology to isolate, expand and supply specific cells which may replace important processes that are deranged or lost in various disease states. Recent approaches are, for example, placing cells on flat sheet membranes, into hollow fibers or encapsulating substances, and to develop bioreactors for the delivery of active cells to a patient.

The kidney is probably the most challenging organ to reconstruct by tissue engineering techniques, because of its complex structure and function. The nephron is the basic structural and functional unit of the kidney. Its chief function is to regulate water and soluble substances by filtering the blood, reabsorbing what is needed and excreting the rest as urine. Nephrons eliminate wastes from the body, regulate blood volume and pressure, control levels of electrolytes and metabolites, and regulate blood pH. Its functions are vital to life and are regulated by the endocrine system by hormones such as antidiuretic hormone, aldosterone, and parathyroid hormone. Each nephron is composed of an initial filtering component (the renal corpuscle) and a tubule specialized for reabsorption and secretion (the renal tubule). The renal corpuscle filters out large solutes from the blood, delivering water and small solutes to the renal tubule for modification.

The most distinctive characteristic of the proximal tubule is its "brush border". The luminal surface of the epithelial cells of this segment of the nephron is covered with densely packed microvilli forming a border readily visible under the light microscope. The microvilli greatly increase the luminal surface area of the cells, presumably facilitating their resorptive function. The cytoplasm of the cells is densely packed with mitochondria in keeping with the energetic requirements of the cells resorptive activity. Fluid in the filtrate entering the proximal convoluted tubule is reabsorbed into the peritubular capillaries, including approximately two-thirds of the filtered salt and water and all filtered organic solutes (primarily glucose and amino acids). This is driven by sodium transport from the lumen into the blood by the $Na^+/K^+$ ATPase in the basolateral membrane of the epithelial cells. Much of the mass movement of water and solutes occurs in between the cells through the tight junctions, which in this case are not selective.

The distal convoluted tubule is similar to the proximal convoluted tubule in structure and function. Cells lining the tubule have numerous mitochondria, enabling active transport to take place by the energy supplied by ATP. Much of the ion transport taking place in the distal convoluted tubule is regulated by the endocrine system. In the presence of parathyroid hormone, the distal convoluted tubule reabsorbs more calcium and excretes more phosphate. When aldosterone is present, more sodium is reabsorbed and more potassium excreted. Atrial natriuretic peptide causes the distal convoluted tubule to excrete more sodium. In addition, the tubule also secretes hydrogen and ammonium to regulate pH. After traveling the length of the distal convoluted tubule, only 3% of water remains, and the remaining salt content is negligible.

So far, human proximal and distal tubule cells, which could be used for clinical approaches to the above described problem, could not successfully be isolated, characterized and kept in culture in their highly differentiated state (for a review on the development of artificial kidneys see Fissell: Development towards an artificial kidney. *Expert Rev. Med. Devices*

2006, 3(2), 155-165). Such cells, however, form the basis for the development of a hybrid human kidney.

Therefore, it was the aim of the present invention to develop a hybrid bioartificial kidney equivalent which is able to replace the main functions, both metabolic and endocrine, of a healthy human renal tubular system.

In 1987, Aebischer et al. first reported the concept of a bioartificial kidney in that tubular epithelial cells formed confluent monolayers on the outer surfaces of a hollow fiber membrane module and had transport ability for water and solutes across the cells and membrane (Aebischer et al.: Renal epithelial cells grown on semipermeable processor. *Trans. Am. Soc. Artif. Intern. Organs* 1987, 33, 96-102; Aebischer et al.: The bioartificial kidney: progress toward an ultrafiltration device with renal epithelial cells processing: *Life Support Sys.* 1987, 5, 159-68). Results achieved by a group around H. David Humes (Humes et al.: Replacement of renal function in uremic animals with a tissue-engineered kidney. *Nature Biotechnology* 17, 451-455, 1999; Humes et al.: Tissue engineering of a bioartificial renal tubule assist device: In vitro transport and metabolic characteristics. *Kidney International* 55, 2502-2514, 1999; Humes et al.: The bioartificial kidney in the treatment of acute renal failure. *Kidney International* 61, S121-S125, 2002; U.S. Pat. No. 6,942,879 B2) show that it is in principle possible to assemble a kind of artificial kidney in the form of an extracorporeal filtration and reclamation circuit which incorporates living epithelial cells of the kidney proximal tubule into its design.

This design is based on an extracorporeal device using a standard hemofiltration cartridge containing approximately $10^9$ renal tubule cells grown as confluent monolayer along the inner surface of the fibers which were coated with an extracellular matrix. The non-biodegradability and the pore size of the hollow fibers allow the membranes to act as scaffolds for the cells and as an immunoprotective barrier. In vitro studies of this renal tubule assist device (RAD) have shown that the cells retain their functionality, referred active transport properties, metabolic activities and important endocrinal processes. The combination of synthetic hemofiltration cartridge in series with this RAD in a second step formulates a tissue-engineered bioartificial kidney which can be used for a more complete renal replacement therapy. In brief, blood enters the fibers of the hemofilter where ultrafiltrate is formed and delivered into the fibers of the tubular lumen in the horizontally oriented RAD. Said ultrafiltrate can be called urine. The filtered blood exiting the hemofilter enters the RAD through the extracapillary space port and disperses among the fibers. At the end of the RAD ultrafiltrate and filtered blood will be collected and the blood is returned to the patient. Heparin is delivered continuously into the blood before entering the RAD to diminish clotting within the device.

The approach of Humes has certain drawbacks, as only proximal tubule cells are used in the design. All other functionally important parts of the tubule system of the kidney, such as the early distal segment, are not available. As described before, the kidney distal segment regulates, for example, the exchange of $Na^+$ for $K^+$ under aldosterone regulation, reabsorption of bicarbonate ion, secretion of hydrogen ion, and conversion of ammonia to ammonium ion. The kidney distal segment is also the place for the formation of other important molecules, such as EGF, cytokines etc. Further, the luminal surfaces of the membranes used by Humes et al. have to be coated e.g. with pronectin-L, a recombinant protein that promotes cell adhesion. It would be preferable, however, to use human proximal and distal epithelial tubule cells instead of animal cells, and to minimize the use of additional, extracorporeal substances in the system, which might promote adverse effects.

In another approach, described e.g. by Saito (Saito A.: Research into the Development of a wearable Bioartificial Kidney with a Continuous Hemofilter and a Bioartificial Tubule Device Using Tubular Epithelial Cells. *Artificial Organs* 2004, 28(1), 58-63), LLC-$PK_1$ cells (porcine kidney cells) and MDCK cells (canine kidney cells) were seeded inside polysulfone or cellulose acetate hollow fibers. Again this tubule device makes use of non-human proximal tubular epithelial cells only. The membranes used were coated with extracellular matrices, and the tubular epithelial cells were transfected with functional genes, such as the rat aquaporin-1 gene (Saito et al.: Present Status and Perspective of the Development of a Bioartificial Kidney for Chronic Renal Failure Patients. 2006, *Therapeutic Apheresis and Dialysis* 10(4), 342-347).

In contrast to the designs of the prior art, the present invention devises an improved hybrid bioartificial kidney in that a proximal and distal unit are combined, thereby further regulating in the distal unit reabsorption of water, sodium chloride and calcium. Further, due to the use of a specifically designed hollow fiber membrane, the culturing of the renal tubular cells can be achieved without additionally coating the membrane with extracorporeal matrices, which is another step closer to the development of an artificial kidney.

SUMMARY OF THE INVENTION

The present invention provides a hybrid bioartificial kidney equivalent which is able to replace the main functions, both metabolic and endocrine, of a healthy human renal tubular system. Another aspect of the invention is a device which can be used for the treatment of acute and chronic renal failure, comprising a hollow fiber membrane lined with human proximal and distal renal tubule cells, preferably in a confluent monolayer.

In the context of the present invention, the term "cell", if not indicated otherwise, shall refer generally to cells of various origin and function, i.e. the term refers both to human and animal cells as well as to cells of different function, differentiation state and morphology. Preferably, the term refers to human cells of all kinds, more preferably to human renal cells. Most preferred are human renal tubule epithelial cells, especially human proximal and distal renal tubule epithelial cells.

The term "confluency" refers to the coverage or proliferation that the cells are allowed over or throughout the culture medium. For example a confluency of 40-60% will mean that there may be little or no restriction to the growth of the cells in/on the medium and they can be assumed to be in a growth phase.

The term "dialysis" refers to the diffusion of solutes along a concentration gradient across a semipermeable membrane, also known as osmosis. In all types of dialysis, blood passes on one side of a semipermeable membrane, and a dialysis fluid is passed on the other side.

The term "membrane" as used herein refers to artificial, semipermeable membranes which are used to separate species in a fluid on the basis of size, charge or other characteristics. The term as used herein, if not specified otherwise, refers to both flat sheet membranes and to hollow fiber membranes. Preferably, the term refers to hollow fiber membranes.

As used herein, the term "sieving coefficient (S)" refers to the physical property of a membrane to exclude or pass molecules of a specific molecular weight. The sieving coefficient can be calculated according to standard EN 1283, 1996.

BRIEF DESCRIPTION OF THE FIGURE

FIG. 1 is a schematic drawing of a device of the invention. The cell-based device comprises a primary dialysis and filtration unit (A), wherein (a) is the line which transports whole blood from the patient (P) to the dialyser. (b) is the line going back to the patient. (c) is a conventional dialyser including a dialysate circuit (d), where the patient's blood is primarily filtrated to produce a primary filtrate. Said filtrate (e) together with a suitable medium (f) enters the secondary metabolic tubular processing unit (B). In this unit, a second dialyser cartridge (g) contains proximal tubule epithelial cells (h) in a first compartment and distal tubule epithelial cells (i) in a second compartment. The cells are located on the inside of the fibers, whereas the patient's blood is flowing on the outside of the fibers (C). The blood is going back to the patient (b), whereas the waste fluid is discarded (j).

DETAILED DESCRIPTION OF THE INVENTION

The present invention provides a hybrid bioartificial kidney equivalent. The present invention also provides a device which can be used for the treatment of acute and chronic renal failure.

Both aspects of the present invention involve a device comprising a first unit for hemodialysis, hemofiltration or hemodiafiltration of blood; and a second unit for processing blood and dialysate from the first unit, comprising a plurality of permselective hollow fiber membranes lined with human proximal tubule cells, and a plurality of permselective hollow fiber membranes lined with human distal renal tubule cells. A example of such a device is shown in FIG. 1. In one embodiment, the human renal tubule cells form a confluent monolayer on the interior surface of the permselective hollow fiber membranes.

In one embodiment, the first unit of the device comprises a plurality of permselective hollow fiber membranes. In a preferred embodiment, the permselective hollow fiber membranes allow for the passage of molecules having a molecular weight of up to 45 kDa in the presence of whole blood, and have a molecular weight exclusion limit in water of about 200 kDa.

The membrane allows for the passage of molecules having molecular weights up to 45 kDa in the presence of whole blood/blood proteins, which means that it has a sieving coefficient (S) of 0.1 to 1.0 in presence of whole blood. for substances having a molecular weight of less than 45 kDa.

A conventional dialyser can be used in the first unit of the device, preferably a high cut-off dialyser such as disclosed in WO 2004/056460, incorporated herein by reference. A suitable high cut-off dialyser is available from Gambro under the trade name HCO 1100™.

In the first unit, the patient's blood is filtrated to produce processed blood and a primary filtrate (dialysate). The blood flows through the lumen of the hollow fiber-containing dialyser, a dialysate fluid is flowing in the opposite direction on the outside of the hollow fibers.

In one embodiment of the device, the first unit comprises an outlet for blood and an outlet for dialysate; and said outlet for blood is connected to the extracapillary space of the permselective hollow fiber membranes of the second unit, and said outlet for dialysate is connected to the intracapillary space of the permselective hollow fiber membranes of the second unit.

The blood processed in the first unit and the primary filtrate (dialysate) are subsequently fed to the second unit. In one embodiment of the invention, the second unit comprises a dialyser cartridge containing proximal tubule epithelial cells (PTECs) in a first compartment and distal tubule epithelial cells (DTECs) in a second compartment. In another embodiment of the invention, the second unit comprises two dialysers filled with PTECs and DTECs, respectively, instead of a two-compartment dialyser.

On the outside of the hollow fibers within the second unit, the dialysate side, the patient's blood is flowing in the opposite direction relative to the primary filtrate inside the hollow fibers. This means that the tubule epithelial cells, first the PTECs and then the DTECs, are exposed to the primary filtrate, which is comparable to the primary urine, which was produced in the first unit, which is thus comparable to the glomerulus. The hollow fibers covered with a PTEC monolayer resemble the proximal tubule, the ones covered with a DTEC monolayer resemble the distal tubule. The functional TECs reabsorb ions and nutrients from the primary filtrate and transport these molecules from the apical (luminal) to the basolateral side of the fiber, which means that the molecules are given back to the patient's blood. Moreover, the TECs exert their metabolic and endocrine functions and convert molecules to certain metabolites and/or secrete substances into the filtrate and blood.

System Design

The system as described before and as shown in FIG. 1 can be based, in principle, on existing dialysis and hemofiltration devices, as long as such devices allow for the control and monitoring of flow rates, filtration rates, volume throughput and pressure in both the primary and secondary unit.

The person skilled in the art is familiar with the design of such dialysis and hemofiltration devices. A variety of suitable designs is used in commercially available dialysers, e.g. the Polyflux® and Revaclear® product lines available from Gambro.

An exemplary dialysis and hemofiltration device comprises two compartments separated by a semipermeable membrane mounted in a casing, a first internal compartment fitted with two accesses and a second external compartment comprising one or two accesses, both compartments being also separated by a potting compound, based on an appropriate adhesive compound, intended for forming as applicable (i) a cylindrical partition separating both compartments of said device containing a semipermeable membrane of the hollow fiber bundle type as defined above or (ii) a tight seal in said device including a semipermeable membrane of the sheet membrane type as defined above.

Another exemplary dialysis and hemofiltration device comprises a plurality of hollow fiber membranes, contained within an outer shell, and configured so that fluid within a space external to the hollow fibers (i.e., an extracapillary compartment) is segregated from fluid passing through the hollow fibers and their corresponding orifices. Additionally, the device includes two manifold end chambers within the outer shell on opposite ends of the device. Each of the two mouths of a hollow fiber connects to a different end chamber. The end chambers and the extracapillary compartment are separated by the semipermeable membranes of the hollow fibers. The composition within the extracapillary compartment can be controlled, to a certain extent, by the molecular weight cutoff, or pore size, of the membranes of the hollow fibers.

For the construction of the secondary device, hollow fiber membranes suitable for the cultivation of adherent renal cells have to be used. Such membranes will be described in detail in the present application. Commercially available examples of dialysis and hemofiltration devices suitable for use in the secondary unit are dialysers available from Gambro under the trade name Nephral® ST.

In addition, further elements are needed for the control and monitoring of specific parameters which are important for the metabolic integrity of the integrated cells, such as oxygen supply, pH, temperature and supply with electrolytes. With regard to the system's application in clinics, it is very important to have a system which will maintain its function under varying temperatures, especially during the steps of cell expansion (room temperature, 20° C.), storage (ca. 4° C.) and application (body temperature, ca. 37° C.). The person skilled in the art will be able to select the appropriate equipment.

The system to be used for the perfusion of the modules containing the cells, i.e. the secondary unit, needs to be built from elements which can be used for cell culture. As is obvious to a person skilled in the art, the pumps which are used have to work in an adequate range. Elements such as tubes, connectors etc. which are in direct contact with the culture media must stand sterilization and have to be stable at 37° C., 5% $CO_2$ and 95% humidity. Further, it is crucial that no toxic substances will leak from these elements into the media. Suitable components are commercially available and known to the person skilled in the art.

Another aspect of the present invention is a system for monitoring the cell culture in hollow fiber (HF) membranes. It is necessary to monitor and control the oxygen and glucose concentration in the HF membranes as well as the hydrodynamic effects of adhesion, proliferation, differentiation and transport function of the tubule epithelial cells in order to build up and maintain the important functions of a bioartificial kidney. In this respect it turned out to be favorable to measure the concentration of glucose, lactate, urea, sodium, potassium, calcium and monitor pH and $pO_2$ of the system, as these parameters allow monitoring the metabolic condition of the cells. It is further desirable to monitor the conductivity of the membrane in order to determine the confluency within the capillary. Suitable equipment for measuring and monitoring these parameters is commercially available and known to the person skilled in the art.

Membranes

In order to be used for the culturing of cells, commercially available membranes usually have to be further modified with additional, generally non-human material, e.g. extracellular matrix components (EMC). Membranes for dialysis are designed to provide high bio-compatibility when in contact with whole blood. This means that they exhibit decreased interaction with blood components such as cells and proteins. It is, however, a prerequisite for the present invention to use a membrane which has a surface that allows cells to adhere, expand and differentiate.

Therefore, particular membranes are used in the present invention. These membranes allow for the cultivation, expansion differentiation, manipulation (e.g. transfection), and storage of adherent renal cells with high performance characteristics without having to pre-treat or pre-coat the membranes with any extracellular matrix components (EMC).

The technology for producing membranes suitable for use in the present invention is based on a generally known phase inversion process using either block-copolymers or polymer alloys consisting of hydrophilic and hydrophobic polymer components. The membranes are formed in precipitating the polymer solution in aqueous fluids. The membrane forming process is controlled by varying critical thermodynamic parameters such as temperature, composition of the polymer solution or composition of the aqueous precipitation bath.

The membranes according to the invention can be sterilized by steam, gamma radiation or ethylene oxide gas without changing permeability or pore size.

In one embodiment of the present invention, the membrane used is a membrane as disclosed in co-pending European Patent Application No. (G 005 P-EP), filed on the same day as the present application, which is incorporated herein by reference.

The membrane is prepared from a copolymer of acrylonitrile and sodium methallylsulfonate. The proportion of sodium methallylsulfonate in the copolymer ranges from 3 to 15 percent by weight. The copolymers usually have a specific viscosity (measured at 25° C. in a dimethyl formamide solution containing 2 g/l) of from 0.1 to 3, preferably 0.5 to 1.5. In one particular embodiment, the copolymer comprises about 3.3 mol-% sulfonic acid groups or sulfonate groups, respectively, and has an average molecular weight of about 250,000 Da. The copolymer is sold by Hospal Industrie under the trade name AN69.

The selectively permeable hollow fibers are of the symmetrical type and have a homogeneous microporous structure, which is substantially uniform throughout their thickness. The average diameter of the micropores is generally less than 100 Å, this average diameter being determined by the method of D. M. Green et al., described in *Trans. Amer. Soc. Artif. Int. Organs,* 1976, 627ff. Moreover, the void factor is most frequently from 40% to 85% and preferably from 60% to 80%. The hollow fibers are generally free of vacuoles (empty spaces included in the wall and having a largest dimension of more than about 5 microns). They do not possess a skin or a dense layer on the surface, either on the inside or on the outside.

In one embodiment, the membrane is coated on one or both faces with polyethyleneimine (PEI). The PEI has an average molecular weight in excess of 25,000 Da, preferably more than 100,000 Da. In one embodiment, a polyethyleneimine having an average molecular weight of 750,000 Da (Lupasol® P, BASF Aktiengesellschaft) is used. In a further embodiment, the PEI is fractionated by ultrafiltration to remove low molecular weight fractions, before it is used for coating the membrane. Details of the ultrafiltration process are disclosed in US 2003/0021826 and WO 01/54802, both incorporated herein by reference. The amount of PEI coated on the membrane ranges from 1 to 80 mg/m$^2$ per face of the membrane.

In addition to the coating with PEI, the membranes optionally are coated with heparin (fractionated or non-fractionated). The surface heparin concentration is between 200 and 20,000 IU/m$^2$, for instance between 500 and 10,000 IU/m$^2$.

In another embodiment of the present invention, the membrane used is a membrane as disclosed in co-pending European Patent Application No. (G 012 P-EP), filed on the same day as the present application, which is incorporated herein by reference.

The membrane contains a combination of polymeric components comprising, as a first polymer component, polysulfone, polyethersulfone or polyarylethersulfone, as a second polymer component polyvinylpyrrolidone, and as a third polymer component polyurethane.

The polymer solution used for preparing the membrane comprises from 11 to 19 wt.-% of a first polymer selected from the group consisting of polysulfone (PS), polyethersulfone (PES) and polyarylethersulfone (PAES), from 0.5 to 13 wt.-% of a second polymer such as polyvinylpyrrolidone (PVP), from 0.001 to 20 wt.-% of a polyurethane (PU), optionally from 0.01 to 2 wt.-% of a polyamide (PA), from 0 to 7 wt.-% of water, and, the balance to 100 wt.-%, of a solvent selected from the group consisting of N-methyl-2-pyrrolidone (NMP), N-ethyl-2-pyrrolidone (NEP), N-octyl-2-pyrrolildone (NOP), dimethyl acetamide (DMAC), dimethyl formamide (DMF), dimethyl sulfoxide (DMSO) and gamma-butyrolactone (GBL).

Said first polymer is preferably present in the polymer solution in an amount of from 13 to 14 wt.-%, especially preferably in an amount of from 13.6 to 14 wt.-%. Polyethersulfone (PES) and polyarylethersulfone (PAES) are preferably used for preparing the membrane of the invention.

Preferably, the polyvinylpyrrolidone (PVP) in the polymer solution consists of a blend of at least two homopolymers of polyvinylpyrrolidone with one of the homopolymers of polyvinylpyrrolidone (=low molecular weight PVP) having an average relative molecular weight of about 10,000 g/mol to 100,000 g/mol, preferably about 30,000 g/mol to 70,000 g/mol, and another one of the homopolymers of polyvinylpyrrolidone (=high molecular weight PVP) having an average relative molecular weight of about 500,000 g/mol to 2,000,000 g/mol, preferably about 800,000 g/mol to 2,000,000 g/mol. Examples for such PVP homopolymers are PVP K85, a high molecular weight PVP having a molecular weight of about 825,000 Da, and PVP K30, a low molecular weight PVP having a molecular weight of about 66,800 Da. In a preferred embodiment, the polymer solution for preparing the membrane comprises from 0.5 to 5 wt.-% of a high molecular weight PVP and from 1 to 8 wt.-% of a low molecular weight PVP.

It is preferred to use, as the polyurethane component, a thermoplastic polyurethane (TPU), more preferably a polyurethane selected from the following group of polyurethanes: DESMOPAN® (Bayer MaterialScience AG), IROGRAN® (Huntsman), ISOPLAST® (The Dow Chemical Company), TECOTHANE® (Velox), CARBOTHANE® (Velox), TECOFLEX® (Velox), ESTANE® (Noveon). Among these polyurethanes, the following types are preferred: DESMOPAN® DP 9665DU, IROGRAN® D74 P 4778, ISOPLAST® 302 EZ, TECOTHANE® TT-1074A, CARBOTHANE® PC-3575A, TECOFLEX® EG-80 HI NCO and ESTANE® 58887 TPU. Polyurethanes which are especially useful for preparing membranes suitable for promoting cell adhesion and proliferation are DESMOPAN® and TECOTHANE® and their specific types mentioned before. The PU content in the solution for preparing the membrane may vary from 0.001 wt.-% to 20 wt.-%. In a preferred embodiment, the solution contains from 0.1 wt.-% to 6 wt.-% of the polyurethane, more preferably from 0.5 wt.-% to 2 wt.-%.

The polymer solution optionally comprises from 0.01 to 2 wt.-%, preferably 0.01 to 0.5 wt.-%, more preferably 0.01 to 0.1 wt.-%, of a polyamide (PA). Preferred polyamides are amorphous polyamides based on trimethylhexamethylendiamine and terephthalic acid, e.g. polyamides available from Degussa/Evonik under the trade name Trogamid®, in particular those of the Trogamid® T series.

The water content of the spinning solution preferably is from 1 to 5 wt.-%, more preferably about 3 wt.-%.

Various solvents can be used for preparing the membrane, such as N-methyl-2-pyrrolidone (NMP), N-ethyl-2-pyrrolidone (NEP), N-octyl-2-pyrrolildone (NOP), dimethyl acetamide (DMAC), dimethyl formamide (DMF), dimethyl sulfoxide (DMSO) or gamma-butyrolactone (GBL) and mixtures thereof. The solvent will be present in an amount representing the balance to 100 wt.-% of the polymer solution. Preferred solvents are N-methyl-2-pyrrolidone (NMP) and dimethyl acetamide (DMAC). N-methyl-2-pyrrolidone (NMP) is especially preferred. The content of the solvent in the polymer solution preferably is from 60 to 80 wt.-%, more preferably from 67 to 76.4 wt.-%.

In still another embodiment of the present invention, the membrane used is a membrane as disclosed in co-pending European Patent Application No. (G 013 P-EP), filed on the same day as the present application, which is incorporated herein by reference.

The membrane is based on a first hydrophobic polymer component, a second hydrophilic polymer component, and, optionally, a third hydrophobic polymer component. The membrane is treated, after preparation, with beta- or gamma-rays or an electron beam at a dose of from 12.5 to 175 kGy in the presence of oxygen.

Preferably the membrane is a polysulfone-, polyethersulfone- or poly(aryl)ethersulfone-based synthetic membrane, comprising, in addition, PVP and optionally low amounts of further polymers, such as, for example, polyamide or polyurethane.

The membrane, during irradiation, may be surrounded by air, wherein oxygen is present during irradiation in a concentration of from 4% to 100%, e.g. 5 to 30% or 15 to 25%, or by water or an aqueous solution comprising low amounts of additives.

In one embodiment, the polymer solution used to prepare the membrane comprises the hydrophobic and hydrophilic polymers in amounts such that the fraction of hydrophobic polymer in the polymer solution is between 5 and 20% by weight and the fraction of the hydrophilic polymer is between 2 and 13% by weight.

Said first hydrophobic polymer is preferably chosen from the group consisting of polyamide (PA), polyaramide (PAA), poly(aryl)ethersulfone (PAES), polyethersulfone (PES), polysulfone (PSU), polyarylsulfone (PASU), polycarbonate (PC), polyether, polyurethane (PUR), polyetherimide and copolymers of said polymers. Said second hydrophilic polymer is preferably chosen from the group consisting of polyvinylpyrrolidone (PVP), polyethylene glycol (PEG), polyglycolmonoester, water soluble cellulosic derivates, polysorbate and polyethylene-polypropylene oxide copolymers. Said third hydrophobic polymer is preferably chosen from the group consisting of polyamide (PA), polyaramide (PAA), poly(aryl)ethersulfone (PAES), polyethersulfone (PES), polysulfone (PSU), polyarylsulfone (PASU), polycarbonate (PC), polyether, polyurethane (PUR), polyetherimide and copolymers of said polymers.

In a first exemplary embodiment, the membrane is prepared from a polymer mixture comprising hydrophobic and hydrophilic polymers in amounts such that the fraction of hydrophobic polymer in the polymer solution used to prepare the membrane is from 5 to 20% by weight and the fraction of the hydrophilic polymer is from 2 to 13% by weight. Said at least one hydrophobic polymer is preferably chosen from the group consisting of polyamide (PA), polyaramide (PAA), polyarylethersulfone (PAES), polyethersulfone (PES), polysulfone (PSU), polyarylsulfone (PASU), polycarbonate (PC), polyether, polyurethane (PUR), polyetherimide and copolymers of said polymers, preferably polyethersulfone or a mixture of polyarylethersulfone and polyamide. Said at least one hydrophilic polymer is preferably chosen from the group consisting of polyvinylpyrrolidone (PVP), polyethylene glycol (PEG), polyglycolmonoester, water soluble cellulosic derivates, polysorbate and polyethylene-polypropylene oxide copolymers, preferably polyvinylpyrrolidone.

A particular example of a membrane which may be used in the context of the present invention comprises, in the polymer solution for preparing the membrane, from 11 to 19 wt.-% of a first polymer selected from the group consisting of polysulfone (PS), polyethersulfone (PES) and polyarylethersulfone (PAES), from 0.5 to 13 wt.-% of a second polymer such as polyvinylpyrrolidone (PVP), from 0 wt.-% to 5 wt.-%, preferably from 0.001 to 5 wt.-% of a polyamide (PA), from 0 to 7 wt.-% of water and, the balance to 100 wt.-%, of a solvent selected from the group consisting of N-methyl-2-pyrrolidone (NMP), which is preferred, N-ethyl-2-pyrrolidone (NEP), N-octyl-2-pyrrolildone (NOP), dimethyl acetamide, dimethyl formamide (DMF), dimethyl sulfoxide (DMSO) and gamma-butyrolactone (GBL).

Preferably, the polyvinylpyrrolidone (PVP) in the polymer solution consists of a blend of at least two homopolymers of polyvinylpyrrolidone with one of the homopolymers of polyvinylpyrrolidone (=low molecular weight PVP) having an average relative molecular weight of about 10,000 g/mol to 100,000 g/mol, preferably about 30,000 g/mol to 70,000 g/mol, and another one of the homopolymers of polyvinylpyrrolidone (=high molecular weight PVP) having an average relative molecular weight of about 500,000 g/mol to 2,000,000 g/mol, preferably about 800,000 g/mol to 2,000,000 g/mol. Examples of such PVP homopolymers are PVP K85, a high molecular weight PVP having a molecular weight of about 825,000 Da, and PVP K30, a low molecular weight PVP having a molecular weight of about 66,800 Da. In a preferred embodiment of the present invention, the polymer solution for preparing the membrane comprises from 0.5 to 5 wt.-% of a high molecular weight PVP and from 1 to 8 wt.-% of a low molecular weight PVP.

Methods for preparing such membranes are described in detail, for example, in U.S. Pat. No. 4,935,141, U.S. Pat. No. 5,891,338 and EP 1 578 521 A1, all of which are incorporated herein by reference. Examples for this type of membrane, which can be effectively treated according to the present invention, are Gambro Polyflux™ membranes (polyarylethersulfone/PVP/polyamide), which are currently used in commercial products, such as, for example, Polyflux™ L and H series; Arylane™ membranes (poly(aryl)ethersulfone/PVP); or DIAPES™ or PUREMA™ membranes (poly(aryl)ethersulfone/PVP) or other commercial dialysis membranes based on blends of hydrophilic and hydrophobic polymers, e.g. blends comprising PVP and PES or polysulfone.

In a second exemplary embodiment, the membrane comprises, in the polymer solution, between 12 and 15 wt.-% of polyethersulfone or polysulfone as hydrophobic polymer and 5 to 10 wt.-% of PVP, wherein said PVP consists of a low and a high molecular PVP component. The total PVP contained in the spinning solution consists of between 22 and 34 wt.-% and preferably of between 25 and 30 wt.-% of a high molecular weight (>100 kDa) component and of between 66 and 78 wt.-%, preferably of between 70 and 75 wt.-% of a low molecular weight (<=100 kDa) component. Examples for high and low molecular weight PVP are, for example, PVP K85/K90 and PVP K30, respectively. The polymer solution, used in the process preferably further comprises 66-86% by weight solvent and 1-5% by weight suitable additives. Suitable additives are, for example, chosen from water, glycerol and/or other alcohols. Water is especially preferred and, when used, is present in the spinning solution in an amount of 1-8% by weight, preferably in an amount of 2-5% by weight.

The solvent used in the process preferably is chosen from the group comprising n-methylpyrrolidone (NMP), dimethylacetamide (DMAC), dimethyl sulfoxide (DMSO), dimethyl formamide (DMF), butyrolactone and mixtures of said solvents. NMP is especially preferred. The center fluid or bore liquid which is used for preparing the membrane comprises at least one of the above-mentioned solvents and precipitation medium chosen from the group of water, glycerol and other alcohols. Most preferably, the center fluid consists of 45-70% by weight precipitation medium, 30-55% by weight of solvent. Preferably, the center fluid consists of 51-57% by weight of water and 43-49% by weight of NMP.

Methods for preparing such membranes are disclosed in detail in European Patent Application No. 08008229, expressly incorporated herein by reference. Examples for this type of membrane are, for example, the Gambro Revaclear™ membrane and derivatives thereof. It is also possible to use, in the context of the present invention, membranes which are currently used in commercial products, such as, for example, the Fresenius FX™-class membranes (Helixone™ membranes) or Optiflux™ type membranes) or other commercial dialysis membranes based on blends of hydrophilic and hydrophobic polymers, e.g. blends comprising PVP and PES or polysulfone.

In a third exemplary embodiment, the membrane comprises, in the polymer solution for preparing the membrane, from 11 to 19 wt.-% of a first polymer selected from the group consisting of polysulfone (PS), polyethersulfone (PES) and polyarylethersulfone (PAES), from 0.5 to 13 wt.-% of a second polymer such as polyvinylpyrrolidone (PVP), from 0.001 to 20 wt.-% of a polyurethane (PU), from 0 to 7 wt.-% water and a solvent selected from the group consisting of N-methyl-2-pyrrolidone (NMP), N-ethyl-2-pyrrolidone (NEP), N-octyl-2-pyrrolildone (NOP), dimethyl acetamide, dimethyl formamide (DMF), dimethyl sulfoxide (DMSO) and gamma-butyrolactone (GBL), adding up to 100 wt.-%.

Said first polymer is preferably present in the polymer solution in an amount of from 13 to 14 wt.-%, especially preferably in an amount of from 13.6 to 14 wt.-%. Polyethersulfone (PES) and polyarylethersulfone (PAES) are preferably used for preparing the membrane. Preferably, the polyvinylpyrrolidone (PVP) in the polymer solution consists of a blend of at least two homopolymers of polyvinylpyrrolidone with one of the homopolymers of polyvinylpyrrolidone (=low molecular weight PVP) having an average relative molecular weight of from about 10,000 g/mol to 100,000 g/mol, preferably about 30,000 g/mol to 70,000 g/mol, and another one of the homopolymers of polyvinylpyrrolidone (=high molecular weight PVP) having an average relative molecular weight of from about 500,000 g/mol to 2,000,000 g/mol, preferably about 800,000 g/mol to 2,000,000 g/mol. Examples of such PVP homopolymers are PVP K85, a high molecular weight PVP having a molecular weight of about 825,000 Da, and PVP K30, a low molecular weight PVP having a molecular weight of about 66,800 Da. In a preferred embodiment, the polymer solution for preparing the membrane comprises from 0.5 to 5 wt.-% of a high molecular weight PVP and from 1 to 8 wt.-% of a low molecular weight PVP. The water content of the spinning solution preferably is from 1 to 5 wt.-%, more preferably about 3 wt.-%. Various solvents can be used for preparing the membrane, such as N-methyl-2-pyrrolidone (NMP), N-ethyl-2-pyrrolidone (NEP), N-octyl-2-pyrrolidone (NOP), dimethyl acetamide, dimethyl formamide (DMF), dimethyl sulfoxide (DMSO) or gamma-butyrolactone (GBL) and mixtures thereof. The solvent will be present in an amount to add up to 100 wt.-% of the polymer solution. The content of the solvent in the polymer solution preferably is from 60 to 80 wt.-%, more preferably from 67 to 76.4 wt.-%.

The membranes as described before are treated by covering them with air, water, or aqueous solutions containing suitable additives, such as, for example, acrylic acid, allylamine or acrylamide in concentrations of from 0.00001 wt.-% to 5 wt.-%, e.g. from 0.0001 to 0.01 wt.-%, and subjecting them to gamma, beta or electron beam irradiation in the presence of oxygen.

To arrive at membranes which may serve for cell culture purposes, membranes are subjected to gamma, beta, or electron beam irradiation, in particular gamma-ray irradiation, using radiation doses of from 12.5 to 175 kGy, with a preference for doses of from 70 to 175 kGy. In another embodiment, the doses used are from 25 to 125 kGy. In yet another embodiment, doses of from 50 to 175 kGy may be used. In yet another embodiment, doses of from 50 to 125 kGy may be used. In yet another embodiment, doses of from 70 to 100 kGy may be used.

In still another embodiment of the present invention, the membrane used is a membrane as disclosed in EP-A 1 875 957, which is incorporated herein by reference.

Said membrane has the smallest pore size on the outer wall surface, and has an outer wall surface which is smooth, continuous and homogeneous on a nanoscopic scale, being virtually devoid of roughness with a roughness parameter $R_a$ and $R_q$ of not more than 100 nm, preferably not more than 10 nm, the roughness being measured using an atomic force microscope (AFM), and the roughness parameters $R_a$ and $R_q$ are calculated using the following equations:

$$R_a = \frac{1}{N} \sum_{i=1}^{N} |Z_i|$$

$$R_q = \sqrt{\frac{1}{N} \sum_{i=1}^{N} Z_i^2}$$

wherein N is the total number of data points and $Z_i$ is the height of a data point above the average picture level. Said smooth outer surface in combination with the polymer system used and the membrane formation conditions is the basis of low thrombogenicity of the membrane. The extremely smooth surface inhibits haemolysis if used in direct blood contact. Blood cells will not be ruptured during the contact with the smooth surface. The smoothness further reduces the interaction with proteins and the adsorption of proteins on the outer surface of the hollow fiber membrane.

The membrane can be prepared by extruding a polymer solution through an outer ring slit of a hollow fiber spinning nozzle, simultaneously extruding a bore liquid through the inner bore of the hollow fiber spinning nozzle, into a precipitation bath. The polymer solution contains 10-20 wt.-% of polysulphone (PSU), polyethersulphone (PES) or polyarylethersulphone (PAES), 2-15 wt.-% polyvinylpyrrolidone (PVP) and a solvent, the bore liquid contains 50-75 wt.-% of a solvent and 25-50 wt.-% of water, and the precipitation bath contains 50-70 wt.-% of a solvent and 30-50 wt.-% of water. The solvent in the polymer solution, the bore liquid and the precipitation bath are chosen from N-methylpyrrolidone, N-ethylpyrrolidone, N-octylpyrrolidone or mixtures thereof, preferably N-methylpyrrolidone.

For obtaining membranes which can be used in the present invention, it is necessary to either (a) add functionalised polymers during the production of the membranes, (b) modify the membranes in situ or (c) treat the membranes with plasma to modify their surface.

Method (a) comprises addition of functionalised polymers during the membrane production process. For obtaining adequate membranes, it is important that the functionalised polymers are compatible with the solution, form a homogeneous blend with the main components, and are only slightly soluble in water. Preferred polymers are (1) carboxylate polysulfone, (2) carboxylate copolymer (butylester of PVM/MA copolymer, CAS Registry Number 009011-16-9) or (3) amino-functionalised polyvinyl alcohol, "amino-PVA".

Method (b) comprises membrane modification in situ, i.e. coating with synthetic or biological substances such as polylysin, polyethylenimin, serum albumin, heparin or fibrin. Membranes are either modified directly without further treatment, or chemically treated before any modification. Such chemical treatment can be, for example, the introduction of functional groups such as carboxyl moieties, which can interact with the coating material.

Method (c) comprises treating the non-modified membranes with different plasma gases, thereby generating an electric charge on the surface of the membrane. Plasma-functionalized membranes are produced by a known plasma technique (Sciarratta et al.: Plasma functionalization of polypropylene with acrylic acid. *Surface and Coatings Technology* 174-175 (2003) 805-810.

Functionalization is achieved by (i) plasma treating, by a soft ionisation plasma process, a mixture comprising a free-radical initiated polymerizable monomer having one or more free-radical polymerizable groups in the presence of a free radical initiator; and (ii) depositing the resulting polymeric coating material produced during step (i) onto the membrane surface.

The process gas for use in the plasma treatment may be any suitable gas but is preferably an inert gas or inert gas based mixture such as, for example helium, a mixture of helium and argon or an argon-based mixture additionally containing ketones and/or related compounds. These process gases may be utilized alone or in combination with potentially reactive gases such as, for example, nitrogen, ammonia, $O_2$, $H_2O$, $NO_2$, air or hydrogen. Most preferably, the process gas will be helium alone or in combination with an oxidizing or reducing gas. The selection of gas depends upon the plasma processes to be undertaken. When an oxidizing or reducing process gas is required, it will preferably be utilized in a mixture comprising 90-99% inert or noble gas and 1 to 10% oxidizing or reducing gas.

The monomers which may be utilised include polymerizable monomers comprising carboxylic acid functionalities, such as methacrylic acid, acrylic acid, alkylacrylic acid, fumaric acid and esters, maleic acid, maleic anhydride, citraconic acid, cinnamic acid, itaconic acid (and esters), vinylphosphonic acid, sorbic acid, mesaconic acid, citric acid, succinic acid, ethylenediamine tetracetic acid (EDTA) and ascorbic acid and their derivatives. Acrylic acid is preferably used.

It is preferable to use methods (a) and (c) for obtaining membranes, as it is one goal of the present invention to avoid any additional material such as fibrin or the like being introduced into the system. Preferably, method (b) will only be used with synthetic coatings, such as polyethyleneimine. Method (c) will most preferably be utilized.

The membrane used in the invention can have any suitable geometry according to the needs of the intended use, i.e. it can be a flat sheet, a hollow fiber or a bundle of hollow fibers, or can be shaped to form chambers or other geometries desired. The core unit comprising the renal cells preferably is a hollow fiber-based membrane system allowing sufficient exchange of $O_2$ and $CO_2$, supply of nutrients and removal of waste products. The surface of the membrane is designed to enable adhesion and proliferation of cells through specific surface characteristics. The advantage of the cultivation of cells inside hollow fibers is based on the advantageous surface to volume ratio which results in the minimization of medium consumption in the cultivation process, the minimization of space requirement and minimization of labor as compared to conventional flask or cell stack culture methods.

In one embodiment, the membrane has an asymmetric structure. In the case of hollow fibers, there is a thin separation layer on the inner side of the fibers. The structure or morphology of the membrane of the invention may otherwise vary without significant impact on its performance regarding cell adhesion and proliferation. The membrane may have, for example, a 3-layer structure or a sponge-like structure or a foam-like structure.

In another embodiment, the hollow fiber membrane wall has at least four layers with different pore sizes and mass densities, wherein the layer positioned closest to the middle of the membrane wall has smaller pore size and a higher mass density than the two layers directly adjacent on both sides, inner and outer side, of this layer. With this structure, physical stability of the membrane is maintained even though the membrane has a small inner diameter and a small wall thickness.

In one embodiment, the hollow fiber membrane has a hydraulic permeability in the range of $1 \cdot 10^{-4}$-$100 \cdot 10^{-4}$ cm$^3$/(cm$^2$ bar s), preferably in the range of $1 \cdot 10^{-4}$ to $70 \cdot 10^{-4}$ cm$^3$/(cm$^2$ bar s), and most preferably in the range of $1 \cdot 10^{-4}$ to $27 \cdot 10^{-4}$ cm$^3$/(cm$^2$ bar s). With this hydraulic permeability the convective transport through the membrane wall is minimized at the same time having high diffusive transport in a broad range with respect to the molecular size (up to 100,000 Da, depending on the fluid and measurement conditions) or shape of the molecule.

In another embodiment, the membrane is a so-called "low flux" membrane. The hydraulic permeability of the membrane may vary from about $0.1 \cdot 10^{-4}$ to $100 \cdot 10^{-4}$ cm$^3$/(cm$^2$ bar sec). In one embodiment, the hydraulic permeability of the membrane is in the range of from $0.1 \cdot 10^{-4}$ to $10 \cdot 10^{-4}$ cm$^3$/(cm$^2$ bar sec), in particular from $0.1 \cdot 10^{-4}$ to $5 \cdot 10^{-4}$ cm$^3$/(cm$^2$ bar sec).

A hollow fiber membrane used in the invention is further characterized by having an inner diameter of from 50 to 2,000 μm, preferably of from 50 to 1,000 μm, and more preferably from 100 to 500 μm. The hollow fiber membrane has a wall thickness of from 10 to 200 μm, preferably of from 20 to 100 μm, and more preferably from 25 to 55 μm.

The thickness of a flat sheet membrane according to the invention may vary between 20 μm and 200 μm. A thickness of 35 μm to 50 μm may be especially advantageous for most applications.

In one embodiment, the membrane used has a polar-dispersive ratio of the lumen side which is >1. Preferably, the polar-dispersive ration of the lumen side is >1.5. The polar-dispersive ratio is determined according to Andrade (Andrade et al.: Surface characterization of poly(hydroxyethyl methacrylate) and related polymers. I. Contact angle methods in water, J. Polym. Sci. Polym. Symp. 1979, Vol. 66, 313). In all measurements done with various membranes, cells showed adequate adhesion to membranes having a polar-dispersive ratio of above 1. Even better results can be achieved with membranes having a polar-dispersive ratio of above 1.5.

The finding that a polymer surface having a certain polar-dispersive ratio can advantageously be used for the culturing of cells can also be used for improving known methods for culturing cells on polymer surfaces. By determining the polar-dispersive ratio of a given polymer surface, such as a flat sheet or hollow fiber membrane, the ability of the cells to adhere to said surface can be assessed without cumbersome and material consuming tests with cells cultures. Accordingly, the present invention also relates to a method for determining the applicability of a given polymer surface for culturing cells by determining the polar-dispersive ratio of the polymer surface. Polymer surfaces which have a polar-dispersive ratio of above 1, preferably above 1.5, are most likely suitable for cell culturing.

Cell Separation and Culture

The ability to isolate and grow cells that possess stem-cell like characteristics with a high capacity for self-renewal and the ability to differentiate these progenitor cells into cells with correct structural and functional morphology in vitro is crucial for providing organ function replacement based on cell therapy.

The present invention uses the isolation and expansion of highly specific human proximal and distal tubule cells from adult tissue, e.g. a segment of nephrectomy. In the present invention, a specific method based on immuno-magnetic techniques is preferably used to isolate proximal and distal human renal tubule cells. The methodology for isolating and expanding renal tubular cells from adult kidneys is disclosed in Kidney Int. 52(5), 1997, 1321-1331.

In a first step, the human tissue parts are mechanically reduced to small pieces with a scalpel and submitted to digestion with collagenase and dispase. After that, the cells are pressed through a cell strainer with 106 μm pores, followed by another digestion with collagenase IV and DNAase. This treatment is followed by a Percoll density gradient centrifugation for 30 minutes at 27,000×g. Finally, immunoglobulin is added.

The separation of the proximal and distal tubular cells is achieved by means of fluorescence-activated cell sorting (FACS). In this method, subpopulations of cells which vary with regard to their phenotype can be sorted by tagging those of interest with an antibody linked to a fluorescent dye. The antibody is bound to a protein that is uniquely expressed in the cells to be separated. The tagged cells are led through a FACS machine. The laser light excites the dye which emits a color of light that is detected by the photomultiplier tube, or light detector. By collecting the information from the light (scattering and fluorescence), a computer can determine which cells are to be separated and collected. For specifically binding the cells on the magnetic beads distal cell monoclonal antibodies against Tamm-Horsfall glycoprotein (THG) and proximal cell monoclonal antibodies against aminopeptidase M (CD13) are used.

The isolated primary proximal and distal tubular cells are cultivated and characterized with various methods such as immunofluorescence, enzyme activity etc. The proximal and distal renal tubular cells are able to take over their role in the production of cytokines, chemokines and other regulatory active substances. Thus, they have the necessary functions needed for a hybrid tubule.

The tubule cells not only possess key transport functions for excretory processes but also provide critical metabolic functions, e.g. glutathione metabolism and ammoniagensis as well as cytokine homeostasis, and endocrinological functions, e.g. vitamin D3 metabolism. The 1-hydroxylation of 25-OH-vitamin D3 in the proximal tubule cell converts vitamin D3 to its most active metabolite. A number of studies have shown that 1,25-dihydroxy vitamin D3 plays an important role in the regulation of the immune system.

The cells in the device of the invention convert 25-OH-calcitriol to 1,25-dihydroxy-calcitriol. The use of renal tubule cells which are able to produce vitamin D3 in a hybrid kidney system of the invention helps to minimize the progression of renal osteodystrophy.

Another aspect of the present invention is a process for producing permselective hollow fiber membranes lined with human proximal or distal renal tubule cells, respectively. The process involves seeding, culturing and expansion of human proximal and distal renal tubular cells, respectively, on the inside of a non-coated hollow fiber membrane, which is water- and solute-permeable, and the formation of a confluent monolayer lining such a membrane.

For this purpose, the cells are expanded ex vivo and, when an appropriate number of cells has been obtained, they are seeded into the hollow fiber.

In a first step of the process, the hollow fiber membrane is seeded with adherent human renal cells, i.e. proximal or distal renal tubule cells. In one embodiment, a suspension of cells in PBS is used for seeding. A suitable concentration of suspended cells is in the range from $0.5 \cdot 10^6$ to $1.0 \cdot 10^6$ cells/ml.

The fluid comprising the suspended seed cells can either be injected into the lumen of the hollow fibers through one of the inlets/outlets of the intracapillary compartment, or circulated through the hollow fibers by means of a pump connected to the inlets/outlets of the intracapillary compartment. In a particular embodiment, the device is simultaneously operated in filtration mode, i.e. fluid is withdrawn from the extracapillary compartment of the device through one of the inlets/outlets of the extracapillary compartment during supply of the seed cell suspension to the lumen of the hollow fibers. Preferably, calcium-free suspension media are used. It has been found that the tendency of thrombus formation can be reduced thereby. Viability of the cells is improved, when in the preparation of the cell suspension, accutase is used for cell separation instead of trypsin, and the temperature of the suspension is kept at 4° C. during the process. To improve uniform distribution of the cells, the device can be shaken or tilted periodically during the seeding process.

After the membrane has been seeded with adherent renal cells, the cells are propagated by culturing them under appropriate conditions using suitable culture media known in the art.

A particularly suitable culture medium for use in a process for expanding adherent renal cells consists of a serum free and animal by-products free basal medium capable of supporting the growth of mammalian epithelial cells in vitro, 20 to 30 μg/ml BPE (Bovine Pituitary Extract), 1 to 20 ng/ml, e.g. 5 ng/ml EGF (Epidermal Growth Factor), 0.5 to 2 mmol/l, e.g. 1.2 mmol/l $Ca^{2+}$, and 0.5 to 3 vol.-%, e.g. 1 vol.-% FCS (Fetal Calf Serum). According to one embodiment, the culture medium consists of a serum free and animal by-products free basal medium capable of supporting the growth of mammalian epithelial cells in vitro, 20 to 30 μg/ml BPE, 5 ng/ml EGF, 1.2 mmol/l $Ca^{2+}$, and 1 vol.-% FCS (Fetal Calf Serum). It has been found that the culture medium improves both the number of cells as well as the cell density of the cultured cells. Additionally, the culture medium improves cell differentiation of cells grown on membranes according to the invention.

In one embodiment of the process, the culture medium is circulated in the extracapillary compartment of the device to supply the cells in the hollow fiber membranes with nutrients and oxygen and to remove metabolites. In another embodiment of the process, culture medium is additionally circulated through the lumen of the hollow fiber membranes.

The hollow fiber has specific characteristics to allow for the adhesion, expansion and functionality of the cells and to fulfill its role in the overall setup.

Therefore, in an embodiment of the present invention, a hollow fiber is used with a specifically designed inner surface which allows for tubule epithelial cell (TEC) adhesion and TEC proliferation while retaining the functionality of the expanded cells. The hollow fiber material preferably has a certain polar-dispersive ratio (p/d ratio) to facilitate cell adhesion and proliferation. The outer surface of the hollow fiber membrane preferably is highly biocompatible (low thrombogenicity, low complement activation, reduced roughness). The hollow fiber membrane further displays a specifically designed porosity and permeability to fulfill its role in transport and supply.

Thus another aspect of the invention is a hollow fiber membrane lined with human proximal and distal renal tubular cells, respectively, preferably in a confluent monolayer.

The TECs in the hollow fiber membranes are able to reabsorb molecules from the filtrate and transcellularly transport these molecules through the membrane to the blood side. A further aspect of the invention, therefore, is a process for the extracorporeal treatment of blood, comprising the steps of (a) subjecting blood to hemodialysis, hemofiltration or hemodiafiltration, thereby producing processed blood and a dialysate;

(b) conducting said dialysate through the intracapillary space of a plurality of permselective hollow fiber membranes lined with human proximal tubule cells, while said processed blood is circulated on the outside of said permselective hollow fiber membranes; and (c) conducting said dialysate through the intracapillary space of a plurality of permselective hollow fiber membranes lined with human distal tubule cells, while said processed blood is circulated on the outside of said permselective hollow fiber membranes.

In one embodiment of the invention, steps (a), (b), and (c) are conducted in sequence, e.g. the dialysate produced in step (a) is first conducted through the lumen of the hollow fiber membranes lined with human proximal tubule cells and subsequently through the hollow fiber membranes lined with human distal tubule cells. In another embodiment, steps (b) and (c) take place simultaneously. In still another embodiment, step (b) takes place after step (c).

EXAMPLES

Viscosity Measurements

The term "viscosity" with respect to the polymer solution of the present invention means the dynamic viscosity, if not otherwise indicated. The unit of the dynamic viscosity of the polymer solution is given in Centipoise (cp) or mPa·s. To measure the viscosity of the polymer solution a commercial rheometer from Rheometic Scientific Ltd. (SR 2000) was used. The polymer solution is placed between two temperature-controlled plates. The measurement is performed at 22° C. All other measurement condition are according to the manufacturer's instructions.

Membrane Bundle Preparation (a) Preparation of Hand Bundles:

The preparation of the membrane bundle after the spinning process of the hollow fiber membranes is necessary to prepare the fiber bundle in an adequate way for succeeding performance tests. The first process step is to cut the fiber bundles to a defined length of 23 cm. The next process step consists of closing the ends of the fibers. An optical control ensures that all fiber ends are closed. Then, the ends of the fiber bundle are transferred into a potting cap. The potting cap is fixed mechanically and a potting tube is put over the potting caps. Afterwards, the potting is done with polyurethane. After the potting it has to be ensured that the polyurethane can harden for at least one day. In the next process step, the potted membrane bundle is cut to a defined length and to open the ends. The last process step consists of visual inspection of the fiber bundle. During this process step, the following points are checked: (1) Quality of the cut (is the cut smooth or are there any damages created by the knife); (2) Quality of the potting (is the number of open fibers of the spinning process reduced by fibers that are potted or are there any visible voids where there is no polyurethane). After the visual inspection, the membrane bundles are stored dry before they are used for the different performance tests.

(b) Preparation of Mini-Modules:

Mini-modules [=fiber bundles in a housing] are prepared by similar process steps. The mini-modules are needed to ensure a protection of the fibers and a very clean manufacturing method as the biocompatibility tests are carried out with human plasma. The manufacturing of the mini-modules differs in the following points: (1) The fiber bundle is cut to a defined length of 20 cm; (2) The fiber bundle is transferred into the housing before closing the fiber ends; (3) The mini-module is put into a vacuum drying oven over night before the potting process.

(c) Preparation of Filters:

The filter (=dialyser) comprises about 8.000 to 10.000 fibers with an effective surface area of 0.5 to 0.6 m². A filter is characterized by a cylindrical housing with two connectors for the dialyzing fluid and applied caps on both sides, each with one centered connector. The manufacturing process (after winding) can be split up into the following main steps: (1) The cut (length of 20 cm) bundles are transferred into the housing with a special bundle claw; (2) Both ends of the bundles are closed; (3) the fibers are potted into the housing with polyurethane (PUR); (4) the ends are cut to open the fibers, wherein a smooth surface is required; (5) Visual inspection of the ends for closed fibers or imperfections in the PUR block; (6) the caps are glued to the connectors.

Example 1

Preparation of Hollow Fiber Membranes

A polymer solution was prepared by mixing 14.0 wt.-% of polyethersulfone (BASF Ultrason 6020), 5.0 wt.-% of PVP K30, 2.0 wt.-% of PVP K85/K90, 3 wt.-% of water and 76.0% of NMP. A mixture of 55 wt.-% water and 45 wt.-% NMP served as center fluid. The viscosity of the polymer solution, measured at a temperature of 22° C., was 5,400 mPa·s.

The center fluid was heated to 55° C. and pumped through a two-component hollow fiber spinneret. The polymer solution was leaving the spinneret through an annular slit with an outer diameter of 0.5 mm and an inner diameter of 0.35 mm. The center fluid was leaving the spinneret in the center of the annular polymer solution tube in order to start the precipitation of the polymer solution from the inside and to determine the inner diameter of the hollow fiber. At the same time, the two components (polymer solution and center fluid) were entering a space separated from the room atmosphere. The space is called spinning shaft. A mixture of steam (100° C.) and air (22° C.) was injected into the spinning shaft. The temperature in the spinning shaft was adjusted to about 45° C. and a relative humidity of 99.5% by the ratio of steam and air. The length of the spinning shaft was 890 mm. By the aid of gravity and a motor-driven roller, the hollow fiber was drawn from top to bottom, from spinneret through the spinning shaft into a water bath in vertical direction. The spinning velocity was 50 m/min. The hollow fiber was subsequently led through a cascade of water baths and temperatures increasing from 15 to 40° C. The wet hollow fiber membrane leaving the water-rinsing bath was dried in a consecutive online drying step. After a texturizing step, the hollow fiber was collected on a spinning wheel in the shape of a bundle.

Example 2

Preparation of Filters

Filters (hollow fibers in a housing) which were subjected to gamma-ray irradiation comprised the hollow fiber membranes of Example 1. The materials for housing, headers, and potting were gamma stable and consisted of Makrolon® DP1-1262 with Fibasol blue (housing/headers) and gamma-stable polyurethane (potting). Filters containing PES/PVP-based membranes (see Example 1) were filled with ambient air and subjected to gamma irradiation from a Co-60 source for 18.9 hours at room temperature, applying a dose of 75 kGy.

Example 3

Preparation of Filters Lined with Adherent Renal Cells

Filters modules prepared according to Example 2 were seeded with human proximal renal tubule epithelial cells (hPTEC) and human distal renal tubule epithelial cells (hDTEC), respectively.

For this purpose, the extracapillary compartment (EC) of the module was washed three times with saline, then filled with saline and sealed. Subsequently, the intracapillary compartment (IC) was flushed with saline. A suspension of cells in PBS having a concentration of 0.5-1.0 Mio cells/ml was prepared and slowly fed to the IC of the module through one of the inlets, while liquid was withdrawn from the EC through one of the outlets. After the total volume of the suspension had been fed to the module, the inlets/outlets of the IC were sealed and perfusion of the culture medium through the EC was started. After 12 hours of perfusion, the IC was rinsed with culture medium for 10 minutes to remove non-adhered cells and then the inlets/outlets of the IC were sealed again.

The EC of the modules was perfused with for 10 days with a medium comprising Keratinocyte-SFM (Invitrogen)+20-30 µg/ml BPE+5 ng/ml EGF+1.2 mmol/l $Ca^{2+}$+1 vol.-% FCS. Starting from day 11, perfusion of the modules with medium was gradually switched to the IC. After 21 days, confluent monolayers had been formed inside the IC of the modules.

Example 4

Conversion of 25-OH-Calcitriol

To test the metabolic functions of the cells within the modules, the conversion of 25-OH-calcitriol to 1,25-dihydroxy-calcitriol was tested with a radioimmunoassay. As is shown in the table below, a significant increase in concentration of the end product could be measured

|  | MTW | Standard Deviation |
|---|---|---|
| Cell extract |  |  |
| control (medium without 25-OH-$D_3$) | 3.6 | 3.2 |
| 10 nmol/l 25-OH-$D_3$/100 ng/ml PTH | 10 | 7.2 |
| 25 nmol/l 25-OH-$D_3$/100 ng/ml PTH | 16.7 | 10.4 |
| 25 nmol/l 25-OH-$D_3$ | 15.7 | 9.8 |

-continued

| Supernatant | MTW | Standard Deviation |
|---|---|---|
| control (medium without 25-OH-D$_3$) | 5 | 3.3 |
| 10 nmol/l 25-OH-D$_3$/100 ng/ml PTH | 8.6 | 2.5 |
| 25 nmol/l 25-OH-D$_3$/100 ng/ml PTH | 9.1 | 0.6 |
| 25 nmol/l 25-OH-D$_3$ | 13.7 | 8.3 |

The tests showed that the hPTECs and hDTECs cultivated in HF membranes maintain their basic functionality.

The invention claimed is:

1. A device comprising
    a) a first unit for at least one of hemodialysis, hemofiltration and hemodiafiltration of blood; and,
    b) a second unit for processing blood and dialysate from the first unit, the second unit comprising
        i) a first plurality of permselective hollow fiber membranes, the insides of which first plurality of hollow fiber membranes are lined with human proximal renal tubule cells, and
        ii) a second plurality of permselective hollow fiber membranes, the insides of which second plurality of hollow fiber membranes are lined with human distal renal tubule cells,
    and wherein the first and second pluralities of permselective hollow fiber membranes are not pretreated with any extracellular matrix components and have polar-dispersive ratios on the lumen side which are greater than 1.

2. The device of claim 1, wherein the first unit comprises a plurality of permselective hollow fiber membranes.

3. The device of claim 2, wherein the permselective hollow fiber membranes permit the passage of molecules having molecular weights of up to 45 kDa in the presence of whole blood, and have a molecular weight exclusion limit in water of about 200 kDa.

4. The device of claim 1 wherein the human proximal renal tubule cells form a confluent monolayer on the interior surface of the permselective hollow fiber membranes lined with human proximal renal tubule cells.

5. The device of claim 1 wherein the human distal renal tubule cells form a confluent monolayer on the interior surface of the permselective hollow fiber membranes lined with human distal renal tubule cells.

6. The device of claim 1 wherein the first unit comprises an outlet for blood and an outlet for dialysate; said outlet for blood is connected to an extracapillary space of the permselective hollow fiber membranes of the second unit, and said outlet for dialysate is connected to an intracapillary space of the permselective hollow fiber membranes of the second unit.

7. The device of claim 1 wherein the permselective hollow fiber membranes in the second unit comprise a copolymer of acrylonitrile and sodium methallylsulfonate, and a polyethyleneimine.

8. The device of claim 1 wherein the permselective hollow fiber membranes in the second unit comprise at least one of a polysulfone, a polyethersulfone and a polyarylethersulfone; a polyvinylpyrrolidone; and a polyurethane.

9. The device of claim 1 wherein the permselective hollow fiber membranes in the second unit have been treated, after preparation of the membranes, with at least one of beta-rays, gamma-rays and an electron beam, at a dose of from 12.5 to 175 kGy, in the presence of oxygen.

10. The device of claim 1 wherein the permselective hollow fiber membranes in the second unit have been treated, after preparation of the membranes, with a plasma comprising a mixture of an inert gas and a polymerizable monomer comprising a carboxylic acid functionality.

11. A method of treatment of at least one of acute and chronic renal failure, the method comprising preparing a device comprising
    a) a first unit for at least one of hemodialysis, hemofiltration and hemodiafiltration of blood; and,
    b) a second unit for processing blood and dialysate from the first unit, the second unit comprising
        i) a first plurality of permselective hollow fiber membranes lined with human proximal renal tubule cells, and
        ii) a second plurality of permselective hollow fiber membranes lined with human distal renal tubule cells, and
    wherein the first and second pluralities of hollow fiber membranes are not pretreated with any extracellular matrix components and have polar-dispersive ratios on the lumen side which are greater than 1, and
    performing the at least one of hemodialysis, hemofiltration and hemodiafiltration of blood with the first unit, and processing blood and dialysate from the first unit with the second unit.

12. A bioartificial kidney equivalent comprising a device comprising
    a) a first unit for at least one of hemodialysis, hemofiltration and hemodiafiltration of blood; and,
    b) a second unit for processing blood and dialysate from the first unit, the second unit comprising
        i) a first plurality of permselective hollow fiber membranes lined with human proximal renal tubule cells, and
        ii) a second plurality of permselective hollow fiber membranes lined with human distal renal tubule cells,
    wherein the first and second pluralities of hollow fiber membranes are not pretreated with any extracellular matrix components and have polar-dispersive ratios on the lumen side which are greater than 1.

13. A process for the extracorporeal treatment of blood, comprising:
    (a) subjecting said blood to at least one of hemodialysis, hemofiltration and hemodiafiltration, thereby producing processed blood and a dialysate;
    (b) conducting said dialysate through the intracapillary space of a first plurality of permselective hollow fiber membranes lined with human proximal renal tubule cells, while circulating said processed blood on the outside of said first plurality of permselective hollow fiber membranes;
    (c) conducting said dialysate through the intracapillary space of a second plurality of permselective hollow fiber membranes lined with human distal renal tubule cells, while circulating said processed blood on the outside of said second plurality of permselective hollow fiber membranes,
    wherein the first and second pluralities of hollow fiber membranes are not pretreated with any extracellular matrix components and have polar-dispersive ratios on the lumen side which are greater than 1.

14. The device of claim 2 wherein the human proximal renal tubule cells form a confluent monolayer on the interior surface of the permselective hollow fiber membranes lined with human proximal renal tubule cells.

15. The device of claim 3 wherein the human proximal renal tubule cells form a confluent monolayer on the interior surface of the permselective hollow fiber membranes lined with human proximal renal tubule cells.

16. The device of claim 2 wherein the human distal renal tubule cells form a confluent monolayer on the interior surface of the permselective hollow fiber membranes lined with human distal renal tubule cells.

17. The device of claim 3 wherein the human distal renal tubule cells form a confluent monolayer on the interior surface of the permselective hollow fiber membranes lined with human distal renal tubule cells.

18. The device of claim 4 wherein the human distal renal tubule cells form a confluent monolayer on the interior surface of the permselective hollow fiber membranes lined with human distal renal tubule cells.

19. The device of claim 14 wherein the human distal renal tubule cells form a confluent monolayer on the interior surface of the permselective hollow fiber membranes lined with human distal renal tubule cells.

20. The device of claim 15 wherein the human distal renal tubule cells form a confluent monolayer on the interior surface of the permselective hollow fiber membranes lined with human distal renal tubule cells.

* * * * *

UNITED STATES PATENT AND TRADEMARK OFFICE
CERTIFICATE OF CORRECTION

PATENT NO. : 8,696,909 B2 Page 1 of 1
APPLICATION NO. : 13/120298
DATED : April 15, 2014
INVENTOR(S) : Luttropp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 297 days.

Signed and Sealed this

Twenty-ninth Day of September, 2015

Michelle K. Lee
*Director of the United States Patent and Trademark Office*